United States Patent [19]

Seal

[11] Patent Number: 5,775,335

[45] Date of Patent: Jul. 7, 1998

[54] APPARATUS TO DIMINISH OR ELIMINATE SNORING

[76] Inventor: Daniel J. Seal, 10201 Wehie Cap Rd., Picayune, Miss. 39466

[21] Appl. No.: 864,837

[22] Filed: May 29, 1997

[51] Int. Cl.[6] .............................. A61F 5/56; A61F 5/08; A61M 15/08; A62B 7/00
[52] U.S. Cl. .............. 128/848; 128/207.18; 128/204.12; 606/204.45
[58] Field of Search ............................ 128/848, 205.25, 128/207.13, 207.18, 204.12; 606/204.45

[56] References Cited

U.S. PATENT DOCUMENTS

| | | | |
|---|---|---|---|
| 2,663,297 | 12/1953 | Turnberg | 128/207.13 |
| 2,672,138 | 3/1954 | Carlock | 128/207.18 |
| 3,424,152 | 1/1969 | Kuhlman . | |
| 4,120,299 | 10/1978 | Nusso . | |
| 4,944,310 | 7/1990 | Sullivan . | |
| 5,301,689 | 4/1994 | Wennerholm . | |
| 5,320,092 | 6/1994 | Ryder | 128/205.25 |
| 5,375,593 | 12/1994 | Press | 128/207.18 |
| 5,425,359 | 6/1995 | Liou | 128/207.13 |
| 5,595,174 | 1/1997 | Gwaltney | 128/207.18 |

*Primary Examiner*—Mickey Yu
*Assistant Examiner*—Dinh Nguyen
*Attorney, Agent, or Firm*—David L. Volk

[57] ABSTRACT

Two cylindrical members having an elongated flexible strap there-between. Each of the members is adapted for insertion into a nostril of a person to enlarge the nostril. Each of the members further comprising a series of longitudinally disposed ridges arranged annularly about the member for comfortably engaging the nostril to prevent accidental removal of the member from the nostril.

5 Claims, 2 Drawing Sheets

APPARATUS TO DIMINISH OR ELIMINATE SNORING

BACKGROUND OF THE INVENTION

1. Field of the Invention

The present invention relates to devices for diminishing or eliminating snoring.

2. Description of the Related Art

Until the present invention, no device has been developed to diminish or eliminate snoring, which is simple to construct, inexpensive, easy to use, durable and effective.

SUMMARY OF THE INVENTION

The apparatus of the present invention includes two cylindrical members having an elongated flexible strap there-between. Each of the members is adapted for insertion into a nostril of a person to enlarge the nostril. Each of the members further comprising a series of longitudinally disposed ridges arranged annularly about the member for comfortably engaging the nostril to prevent accidental removal of the member from the nostril.

Thus, the present invention is simple to construct, inexpensive, easy to use, durable and effective. Still further features and advantages will become apparent from the ensuing description and drawings.

DETAILED DESCRIPTION

Figure 1:
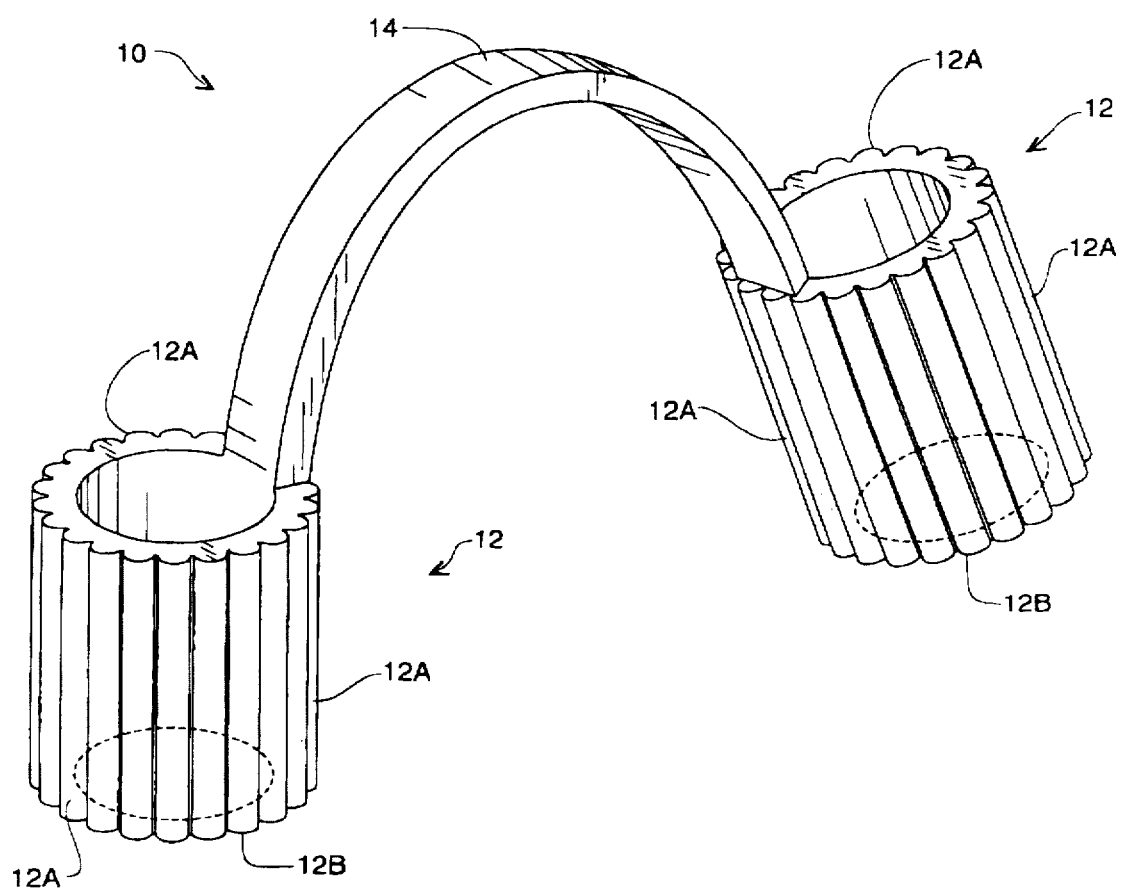
FIG. 1 is a perspective view of the apparatus to diminish or eliminate snoring of the present invention.

FIG. 1 is a perspective view of the apparatus 10, which comprises two elongated cylindrical members 12 having an elongated flexible strap 14 there-between. Each of the members 12 comprises a series of longitudinally disposed ridges 1 2A arranged annularly about the member 12.

Figure 2:
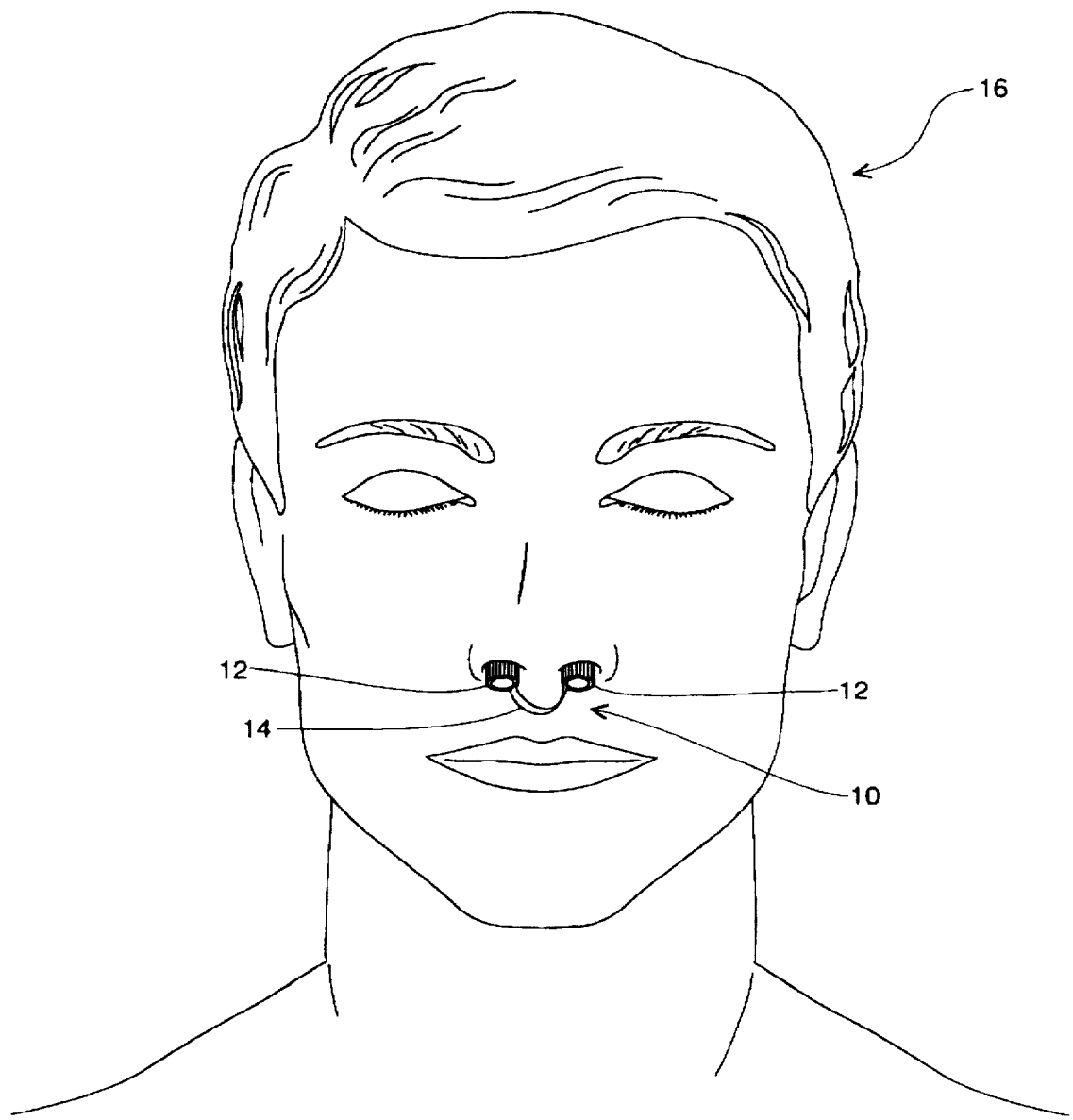
FIG. 2 is a perspective view of the apparatus in use.

FIG. 2 is a perspective view of the apparatus 10 in use by a sleeping person 16 to diminish or eliminate snoring. Referring to FIGS. 1 and 2, to use the invention, free ends 12B of the members 12 are inserted into nostrils of the person 16. This has the effect of slightly enlarging the nasal passages, thus permitting easier, more even breathing, and thus reducing or eliminating snoring in many people. The hollow shape of the members 12 permits air passage through the members 12. The ridges 12A have the effect of comfortably engaging the members 12 within the nostrils of the person 16 to help prevent accidental removal of the members 12 from the nostrils. The longitudinal disposition of the ridges 12A provides smooth and comfortable insertion and removal of the members 12, while still providing an engaging effect within the nostrils.

The foregoing description is included to describe embodiments of the present invention which include the preferred embodiment, and is not meant to limit the scope of the invention. From the foregoing description, many variations will be apparent to those skilled in the art that would be encompassed by the spirit and scope of the invention. Accordingly, the scope of the invention is to be limited only by the following claims and their legal equivalents.

The invention claimed is:

1. A device to assist in diminishing snoring comprising two hollow, tubular members having an elongated connector there-between, each of the members adapted for insertion into a nostril of a person to enlarge the nostril, each of the members further comprising a series of longitudinally disposed ridges integrally formed on an outer surface of the member and arranged annularly about the member, for comfortably engaging the nostril to prevent accidental removal of the member from the nostril.

2. The device of claim 1, wherein the device is constructed of rubber.

3. A device to assist in diminishing snoring comprising two hollow, cylindrical members having an elongated flexible strap there-between, each of the members adapted for insertion into a nostril of a person to enlarge the nostril, each of the members further comprising a series of longitudinally disposed ridges integrally formed on an outer surface of the member and arranged annularly about the member, for comfortably engaging the nostril to prevent accidental removal of the member from the nostril.

4. The device of claim 3, wherein the device is constructed of rubber.

5. A device to assist in diminishing snoring comprising two hollow, tubular members having an elongated connector there-between, each of the members adapted for insertion into a nostril of a person to enlarge the nostril, each of the members further comprising at least one longitudinally disposed ridge integrally formed on an outer surface of the member, the ridge having a height which is substantially constant along an entire length of the ridge, the ridge extending substantially along an entire length of the member, the ridge for comfortably engaging the nostril to prevent accidental removal of the member from the nostril.

* * * * *